(12) United States Patent
Kang et al.

(10) Patent No.: US 9,581,577 B2
(45) Date of Patent: Feb. 28, 2017

(54) MINIATURIZED FLOW-THROUGH CELL

(71) Applicants: Lifeng Kang, Singapore (SG); Jaspreet Singh Kochhar, Singapore (SG); Choon Siong Mah, Singapore (SG)

(72) Inventors: Lifeng Kang, Singapore (SG); Jaspreet Singh Kochhar, Singapore (SG); Choon Siong Mah, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 363 days.

(21) Appl. No.: 14/051,720

(22) Filed: Oct. 11, 2013

(65) Prior Publication Data
US 2014/0102177 A1 Apr. 17, 2014

Related U.S. Application Data

(60) Provisional application No. 61/712,903, filed on Oct. 12, 2012.

(51) Int. Cl.
*G01N 33/15* (2006.01)
*C12M 1/12* (2006.01)
*G01N 13/00* (2006.01)

(52) U.S. Cl.
CPC ............ *G01N 33/15* (2013.01); *G01N 13/00* (2013.01); *G01N 2013/003* (2013.01)

(58) Field of Classification Search
CPC ....... G01N 33/15; G01N 13/00; G01N 13/003
See application file for complete search history.

(56) References Cited

U.S. PATENT DOCUMENTS

| | | | | |
|---|---|---|---|---|
| 5,198,109 A | * | 3/1993 | Hanson ................. | G01N 13/00 210/321.75 |
| 2005/0019903 A1 | * | 1/2005 | Yang ..................... | G01N 13/00 435/288.2 |
| 2005/0191338 A1 | * | 9/2005 | Kang ................... | A61K 9/0014 424/449 |

* cited by examiner

*Primary Examiner* — Michael Hobbs
(74) *Attorney, Agent, or Firm* — Ming Chow; Sinorica, LLC

(57) ABSTRACT

The present disclosure relates to a diffusion cell for testing the permeation of a compound(s) across a membrane. Also, the present disclosure relates to a method of manufacturing a diffusion cell. Further, the present disclosure relates to a method of performing an assay using a diffusion cell.

8 Claims, 12 Drawing Sheets

MINIATURIZED FLOW-THROUGH CELL

CROSS REFERENCE TO RELATED APPLICATIONS

This application claims priority to the U.S. Provisional Application No. 61/712,903, entitled "A Miniaturized Flow-Through Cell (MFtC) for Testing the Permeation of Drugs across Biological Membranes" filed on Oct. 12, 2012.

TECHNICAL FIELD

The present disclosure generally relates to diffusion cells. In particular, the present disclosure relates to diffusion cells for testing the permeation of compounds across membranes.

BACKGROUND

Breast cancer is the most commonly diagnosed cancer in women worldwide with about 1.38 million newly diagnosed cases each year. Nearly 70% of breast cancer patients are hormone-receptor positive. For these patients, tamoxifen has been the most widely used adjuvant endocrine therapy. While tamoxifen is effective, it is a pro-drug that requires extensive CYP2D6 metabolism into active metabolites such as endoxifen (ENX) (FIG. 1). Recently, it has been reported that genetic polymorphism in CYP2D6 can impair the biotransformation of tamoxifen into its active metabolites. To overcome the poor outcomes associated with breast cancer therapy for patients with reduced CYP2D6 activity, direct administration of endoxifen has been advocated. Clinical trials are currently being conducted on the oral use of endoxifen as the hydrochloride salt form.

Apart from the oral route, transdermal drug delivery of the endoxifen has also been explored. However, studies have shown a limited drug flux through skin. Based on the required daily dose of endoxifen, therapeutically relevant concentrations of endoxifen have not been achieved via transdermal drug delivery. Therefore, further studies are needed for the effective delivery of endoxifen through skin. Moreover, a transdermal gel of 4-hydroxy metabolite of tamoxifen is currently under phase 2 clinical trials, indicating the potential for transdermal administration of active metabolites like endoxifen in the management of breast cancer.

The delivery of drugs and/or cosmetics through skin is an alternative route to painful injections. The transdermal delivery market was valued at about $21.5 billion in 2010 and is predicted to reach about $31.5 billion by 2015. The annual U.S. market for transdermal patches is estimated to be more than about $3 billion. Transdermal drugs account for more than about 12% of the global drug delivery market.

Conventionally, a variety of transdermal diffusion cells have been developed for the evaluation or testing of in vitro permeation characteristics of transdermally delivered drugs. In principle, some of the transdermal diffusion cells developed are based on the static, non flowing cells in which the donor and receptor compartments can be placed either vertically (Franz type) or horizontally (side-by-side). Some of the transdermal diffusion cells developed are in-line, flow through cells that offer the advantage of continual replenishment of receptor fluid and hence aid in maintaining a condition similar to microcirculation in the in vivo setting.

Several modified versions of these diffusion cells have also been fabricated and validated against the conventional apparatuses. For example, the permeation characteristics of hydrocortisone were compared using the "enhancer cell", which is a modified version of a USP type II dissolution apparatus serving as a diffusion cell. Modified automatic sampling apparatuses have also been developed. These static and flow-through cells have been compared and validated.

However, a major drawback of the above mentioned cells and known commercial cells such as the ILC14 Automated System from PermeGear Inc., the SYSTEM 912-24 from Logan Instruments Corp, and Vertical/horizontal diffusion cells from Shanghai Kaikai Science and Technology Trade Ltd. is the requirement of relatively large amounts of the drug(s) to be tested and relatively large areas and/or amounts of membrane (e.g., skin). Typically, this major drawback is largely due to the inherent design of the cells and systems.

Endoxifen's physicochemical properties make it a good candidate for transdermal delivery. However, as an investigative drug, its limited supply and high cost make it difficult to conduct extensive pre-formulation studies.

Similarly, other investigational new drug entities are also available in limited supply and are also prohibitively expensive. This makes it difficult to conduct extensive pre-formulation studies, particularly those requiring large amounts of the drugs, such as, in vitro permeation studies through the skin to evaluate the transdermal drug delivery potential of a drug candidate. With the economic environment in pharmaceutical firms becoming more tenuous and pharmaceutical cost containment becoming a main focus, the need to develop pre-formulation testing systems that utilize minimum amounts of the drugs to be tested is the need of the hour. As mentioned above, a major drawback of current known cells/systems due to their inherent design is the requirement of relatively large amounts of the drug to be tested and relatively large areas/amount of membranes (e.g., skin).

Thus, there is a need to provide a diffusion cell and/or diffusion cell system that avoids or at least ameliorates one or more of the disadvantages described above.

SUMMARY

A first aspect of the present disclosure provides a diffusion cell that can comprise: a donor compartment; a receptor compartment, wherein the receptor compartment comprises a first opening and a second opening; a tube, wherein the tube extends through a vertical axis of the receptor compartment, wherein the tube comprises a length, wherein the tube comprise a first end and a second end, wherein the first end of the tube extends through the first opening of the receptor compartment, wherein the second end of the tube extends through the second opening of the receptor compartment. In some embodiments, the tube can comprise a split or slit.

In some embodiments, the donor compartment can comprise a first end and a second end, wherein the donor compartment comprises a cavity extending along a vertical axis of the donor compartment, wherein the cavity of the donor compartment comprises a first end and a second end, wherein the first end of the cavity of the donor compartment forms a first opening in the first end of the donor compartment, and wherein the second end of the cavity of the donor compartment forms a second opening in the second end of the donor compartment.

In some embodiments, the receptor compartment can comprise a cavity, wherein the cavity of the receptor compartment comprises an open end and a closed end.

In some embodiments, the second end of the donor compartment can be adjacent to the closed end of the cavity of the receptor compartment.

In some embodiments, the second opening in the second end of the donor compartment can be adjacent to the split or slit of the tube.

In some embodiments, the donor compartment can be made from a material comprising polydimethylsiloxane. In some embodiments, the receptor compartment can be made from a material comprising polydimethylsiloxane.

In some embodiments, the tube can be made from a material comprising a plastic.

In some embodiments, the diffusion cell described above can be miniaturized. In some embodiments, the receptor compartment can comprise a height of about 15 mm to about 17 mm (e.g., 16 mm) and a width of about 22 mm to about 23 mm (e.g., 22 mm). In some embodiments, the donor compartment can comprise a height of about 12 mm to about 14 mm (e.g., 13 mm) and a width of about 16 mm to about 17 mm (e.g., 16 mm).

In some embodiments, the first end of the tube can be connected to a controllable receptor solution introducer. In some embodiments, the controllable receptor solution introducer can be connected to a pump.

In some embodiments, the second end of the tube can be connected to a sampling container.

A second aspect of the present disclosure provides a method of manufacturing a diffusion cell, wherein the method can comprise: providing a first well; inserting a first mold into the first well, wherein a first cavity space is formed between the first mold and the first well; filling the first cavity space formed between the first mold and the first well with a first material, wherein the first material is cured to form a receptor compartment; removing the first mold; providing a second well; inserting a second mold into the second well, wherein a second cavity space is formed between the second mold and the second well; filling the second cavity space formed between the second mold and the second well with a second material, wherein the second material is cured to form a donor compartment; and removing the second mold.

In some embodiments, the filling of the first cavity space with the first material can result in the formation of the receptor compartment comprising a cavity, wherein the cavity of the receptor compartment comprises an open end and a closed end. In some embodiments, the first material can comprise polydimethylsiloxane.

In some embodiments, the filling of the second cavity space with the second material can result in the formation of the donor compartment comprising a first end and a second end, wherein the donor compartment comprises a cavity extending along a vertical axis of the donor compartment, wherein the cavity of the donor compartment comprises a first end and a second end, wherein the first end of the cavity of the donor compartment forms a first opening in the first end of the donor compartment, and wherein the second end of the cavity of the donor compartment forms a second opening in the second end of the donor compartment. In some embodiments, the second material can comprise polydimethylsiloxane.

In some embodiments, the method of manufacturing a diffusion cell described above can further comprise: placing the donor compartment within the receptor compartment.

In some embodiments, the method of manufacturing a diffusion cell described above can further comprise placing a tube within the first well, wherein the tube extends through a vertical axis of the first well.

In some embodiments, the first well can comprise a tube, wherein the tube extends through a vertical axis of the first well.

In some embodiments, the method of manufacturing a diffusion cell described above can comprise boring a tube manually through a vertical axis of the receptor compartment.

In some embodiments, the tube can be integrally formed as a part of the receptor compartment.

In some embodiments, the filling of the first cavity space with the first material can result in the formation of the receptor compartment comprising the tube extending through a vertical axis of the receptor compartment.

In some embodiments, the tube comprises a length, wherein the tube comprise a first end and a second end, wherein the first end of the tube extends through a first opening of the receptor compartment, wherein the second end of the tube extends through a second opening of the receptor compartment.

In some embodiments, the method of manufacturing a diffusion cell described above can further comprise connecting the first end of the tube to a controllable receptor solution introducer.

In some embodiments, the method of manufacturing a diffusion cell described above can further comprise connecting the controllable receptor solution introducer to a pump.

In some embodiments, the method of manufacturing a diffusion cell described above can further comprise connecting the second end of the tube to a sampling container.

In some embodiments, the material used to manufacture the receptor compartment can comprise polydimethylsiloxane. In some embodiments, the material used to manufacture the donor compartment can comprise polydimethylsiloxane.

In some embodiments, the diffusion cell can be miniaturized.

A third aspect of the present disclosure provides a method of performing an assay, wherein the method can comprise: providing a diffusion cell, wherein the diffusion cell comprises: a donor compartment; a receptor compartment, wherein the receptor compartment comprises a first opening and a second opening; a tube, wherein the tube extends through a vertical axis of the receptor compartment, wherein the tube comprises a length, wherein the tube comprise a first end and a second end, wherein the first end of the tube extends through the first opening of the receptor compartment, wherein the second end of the tube extends through the second opening of the receptor compartment, wherein the tube comprises a split or slit.

In some embodiments, the method of performing an assay can comprise: placing a membrane on top of the split or slit of the tube. In some embodiments, the membrane can comprise a biological membrane and/or a synthetic membrane.

In some embodiments, the method of performing an assay can comprise: mounting or placing a membrane between the donor compartment and the receptor compartment. In some embodiments, the membrane can comprise a biological membrane and/or a synthetic membrane.

In some embodiments, the method of performing an assay can further comprise: placing the donor compartment within the receptor compartment, wherein the donor compartment sits on the membrane.

In some embodiments, the tube can comprise a channel, wherein the split or slit comprises a first open end and a second open end, wherein the first open end faces the donor compartment, wherein the second open end faces the channel, wherein the method can further comprise: placing a donor solution into the donor compartment, wherein the donor solution permeates through the membrane to form a permeate solution, wherein the permeate solution enters the first open end of the slit and passes through the second open end of the slit into the channel of the tube.

In some embodiments, the donor solution can comprise a volume of about 70 µl to about 300 µl (e.g., 70 µl).

In some embodiments, the first end of the tube can be connected to a controllable receptor solution introducer, wherein the controllable receptor solution introducer is connected to a pump, wherein a receptor solution is placed in the controllable receptor solution introducer, wherein the pump controls a flow rate of the receptor solution.

In some embodiments, the pump can provide a flow rate of about 0.828 µl/hr to about 1270 ml/hr (e.g., 0.18±0.01 ml/hr or 0.2 ml/hr).

In some embodiments, the second end of the tube can be connected to a sampling container, wherein the pump circulates the receptor solution through the channel of the tube, wherein the receptor solution in the channel of the tube carries the permeate solution in the channel of the tube to the sampling container forming a sample.

BRIEF DESCRIPTION OF THE DRAWINGS

FIG. 4A is an image of a MFtC having vacuum grease applied, wherein the MFtC shows no leakage after 0 hours of a permeation study. FIG. 4B is an image of the MFtC having vacuum grease applied, wherein the MFtC shows no leakage after 48 hours of the permeation study. FIG. 4C is an image of a MFtC having no vacuum grease applied, wherein the donor solution started leaking after a few hours of a permeation study.

DETAILED DESCRIPTION

Figure 1:
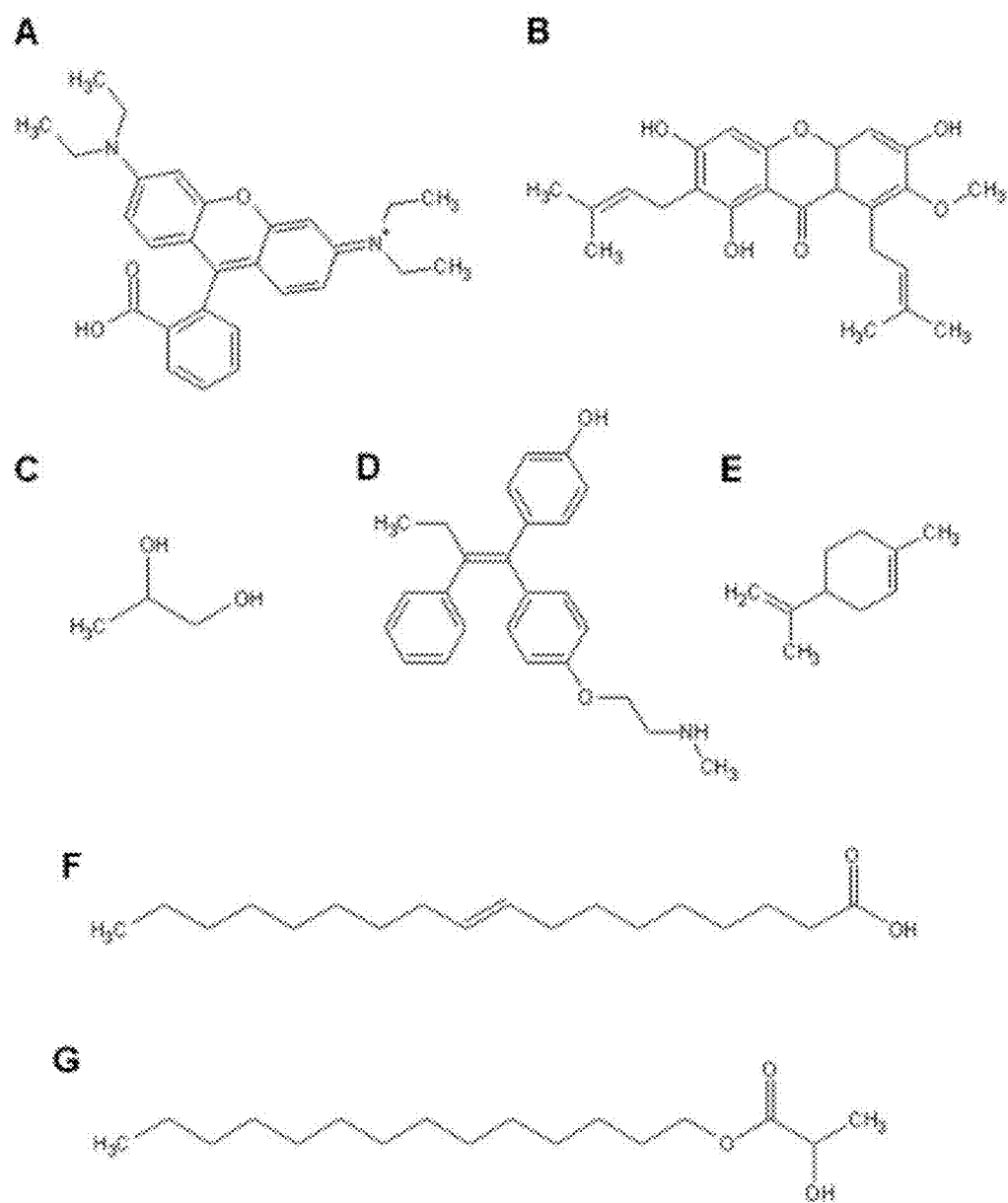
FIG. 1 illustrates chemical structures of (A) mangostin (MW=410.46, log P=6.64), (B) rhodamine B (MW=479.02, log P=2.43), (C) propylene glycol (MW=76.09, log P=−1.00), (D) endoxifen (MW=373.49, log P=4.94), (E) limonene (MW=136.2, log P=4.83), (F) oleic acid (MW=282.46, log P=7.42) and (G) myristyl lactate (MW=286.45, log P=6.08).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein.

Unless specified otherwise, the terms "comprising" and "comprise" as used herein, and grammatical variants thereof, are intended to represent "open" or "inclusive" language such that they include recited elements but also permit inclusion of additional, un-recited elements. The use of "/" in a FIG. or associated text is understood to mean "and/or" unless otherwise indicated. As used herein, the term "about", in the context of concentrations of components, conditions, other measurement values, etc., means+/−5% of the stated value, or +/−4% of the stated value, or +/−3% of the stated value, or +/−2% of the stated value, or +/−1% of the stated value, or +/−0.5% of the stated value, or +/−0% of the stated value.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Throughout this disclosure, certain embodiments can be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The present disclosure relates to a miniaturized flow-through diffusion cell (MFtC) that utilizes a minimal amount of a drug for in vitro skin permeation studies.

The present disclosure relates to a miniaturized flow-through cell (MFtC) that can utilize microliter volumes of the candidate drugs to be tested. In accordance with an embodiment of the present disclosure, an MFtC can be made from a biomaterial such as polydimethylsiloxane (PDMS). In accordance with an embodiment of the present disclosure, an MFtC can be manufactured using simple polydimethylsiloxane (PDMS) molding techniques to cast donor and receptor compartments. Due to the flexible nature of PDMS, this novel approach of fabricating flow through cells can be easily customized to the requirements of permeation studies.

The validation of the MFtC against established horizontal (static) diffusion cells yielded similar permeation parameters for drugs with different properties. In some embodiments, a MFtC of the present disclosure can be adaptable to both thin skin types (i.e., rat skin) and thick skin types (i.e., pig skin), making it a versatile system for pre formulation studies. In some embodiments, a MFtC of the present disclosure can be adaptable to other animal skin types, human skin and/or other membranes, such as, biological membranes and/or synthetic membranes.

In some embodiments, a MFtC of the present disclosure can be fabricated for in vitro skin permeation studies. An embodiment of a MFtC and/or MFtC system of the present disclosure was compared and validated against a static, horizontal diffusion cell (HDC) using two model drugs, namely, rhodamine B and α-mangostin. In the present disclosure, histological sectioning of the skin 24-48 hr post-application in both diffusion cells was conducted to test for skin damage. Subsequently, the skin permeation of endoxifen was assessed with several skin permeation enhancers (PEs). One of the enhancers was found to be able to deliver enough endoxifen for its clinical applications.

The miniaturized flow-through cells (MFtCs) of the present disclosure have been validated against horizontal diffusion cells and have been shown to cause no noticeable damage to the applied skin, as observed by histological sectioning. The MFtCs of the present disclosure were also shown to be useful for searching for suitable enhancers for endoxifen. Endoxifen permeation using permeation enhancers was tested by using a MFtC of the present disclosure and limonene was found to achieve the highest flux, attaining the requirement for clinical applications. The MFtC of the present disclosure can thus be useful in carrying out pre-formulation studies for expensive, new drug entities, in industrial research as well as academic research.

In some embodiments, a MFtC of the present disclosure can be used for permeation testing of drug compounds, model compounds, model drug compounds, vehicles, carriers, drug vehicles, drug carriers, active compounds, active agents, cosmetic compounds, permeation enhancers and/or other compounds.

The present disclosure also relates to a novel pre-formulation testing system that utilizes a minimum amount of candidate drugs for in vitro skin permeation studies.

EXAMPLES

1. Materials and Methods 1.1. Materials

Rhodamine B and sodium azide were obtained from Alfa Aesar, UK. Phosphate buffered saline (PBS) (10×) was obtained from Vivantis, Malaysia. Propylene glycol was obtained from Chempure, Singapore. Polydimethylsiloxane (PDMS) (Sylgard 184 Silicone Elastomer Kit) was obtained from Sylgard, USA. Methanol for HPLC was purchased from Tedia, USA. Endoxifen hydrochloride, (R)-(+)-limonene and oleic acid were obtained from Sigma-Aldrich, USA. Myristyl lactate was obtained from Chemic Laboratories, USA. An α-mangostin standard was supplied by Dr. Prachya Kongtawelent from Chiang Mai University, Thailand. All PBS solutions used in the permeation experiments contained 0.005% of sodium azide as anti-microbial agent. Ultrapure water (Millipore, USA) was used in the preparation of aqueous solutions. The above-mentioned chemicals and/or materials can be provided by other suppliers as needed or per application requirements.

1.2. Fabrication of Miniaturized Flow-Through Cell (MFtC)

Figure 2A:
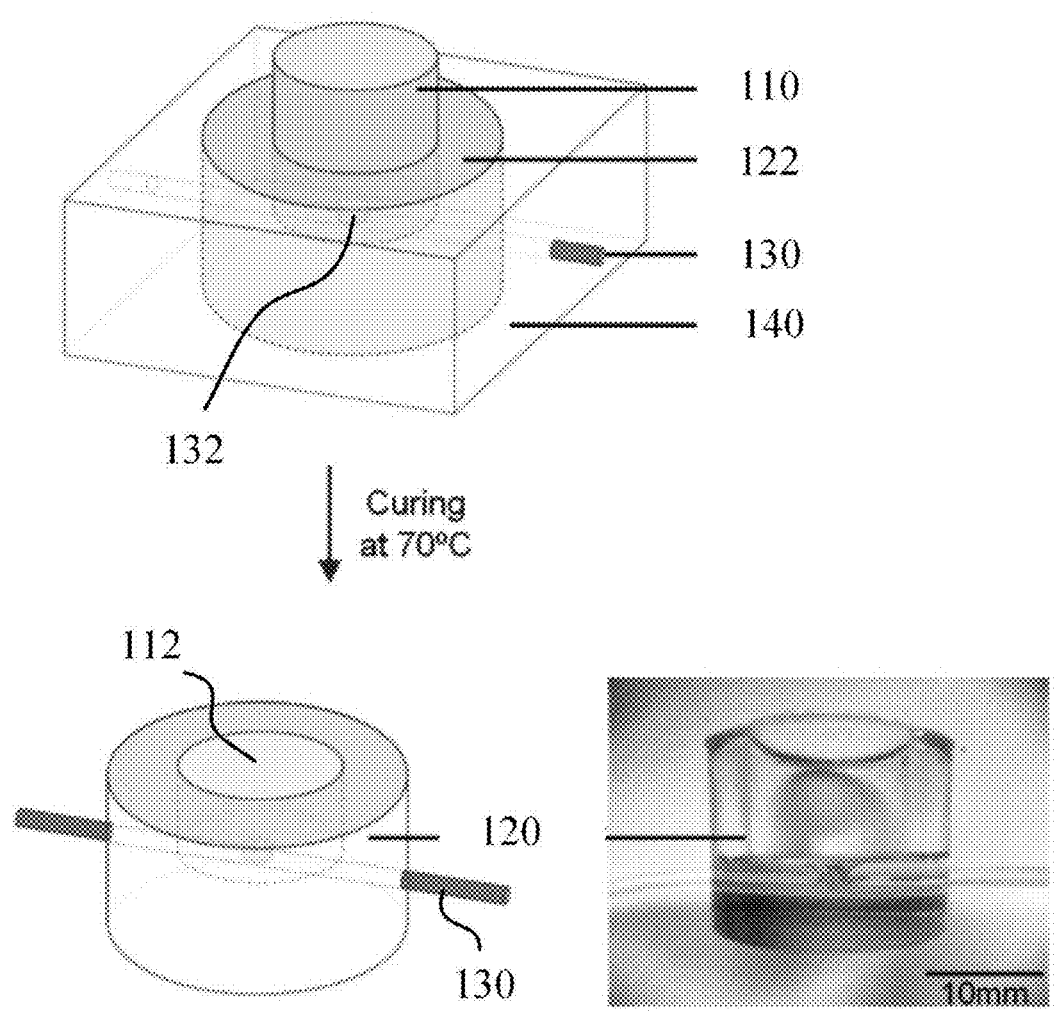
FIG. 2A is a schematic diagram of a fabrication process of a receptor compartment in accordance with an embodiment of the present disclosure.

In accordance with an embodiment of the present disclosure, the process or method of fabricating a MFtC 5 involved two simple PDMS molding steps. Firstly, referring to FIG. 2A, for fabricating the receptor compartment 120 (16 mm tall, 22 mm wide), a specially designed borosilicate glass mold 110 (16 mm wide) was inserted into a single well of a 12-well plate 140 (Cellstar, Greiner Bio-One), carrying a 0.9 mm poly vinyl chloride tube 130 or tubing 130 (B. Braun, Germany) bore through a vertical axis of the single well. In some embodiments, other well plates 140 having different numbers of wells can be contemplated for large scale manufacturing purpose. The borosilicate glass mold 110 sits firmly in and/or on a small slit 132 or small split 132 created in the tube 130 or tubing 130. In some embodiments the slit 132 or split 132 can have a length of about 1.5 mm to about 2.5 mm and a width of about 1.5 mm to about 2.5 mm and a depth of about 0.7 mm to about 1.2 mm. The depth of the slit 132 or split 132 is dependent on the size of the bore of the tube 130 or tubing 130 and/or the diameter of the tube 130 or tubing 130. In some embodiments, the bore of the tube 130 or tubing 130 and/or the diameter of the tube 130 or tubing 130 can be about 0.9 mm. In some embodiments, the bore of the tube 130 or tubing 130 and/or the diameter of the tube 130 or tubing 130 can be about 0.7 mm to about 1.2 mm. PDMS was then filled into the cavity 122 between the glass mold 110 and the well plate 140, and subsequently cured at 70° C. for 2 hr. The glass mold 110 was then removed to create a hollow cavity 112 for a donor compartment 220 to sit in. In some embodiments, the slit 132 or split 132 can be a perforation 132 or a hole 132.

In some embodiments, the size of the receptor compartment 120 and the mold of the receptor compartment 110 of the present disclosure can be modified as needed or per application requirements. In some embodiments, the shape of the receptor compartment 120 and the mold of receptor compartment 110 can be cylindrical or cuboidal. Other shapes are also contemplated. In some embodiments, the mold of receptor compartment 110 of the present disclosure can be made from other materials such as metal, plastic, etc. In some embodiments, the diameter and the material of the tube 130 or tubing 130 that is bored through the vertical axis of the well and/or that is extending through a vertical axis of the receptor compartment 120 can be modified as needed or per application requirements.

In some embodiments, the tube 130 or tubing 130 can be integrally formed as a part of the receptor compartment 120. In some embodiments, the tube 130 or tubing 130 can be manually bored through the receptor compartment 120.

In some embodiments, the slit 132 or split 132 can be created in the tube 130 or tubing 130 prior to placing the tube 130 or tubing 130 in the well of the well plate 140. In some embodiments, the slit 132 or split 132 can be created in the tube 130 or tubing 130 prior to boring the tube 130 or tubing 130 through a vertical axis of the well of the well plate 140. In some embodiments, the slit 132 or split 132 can be created in the tube 130 or tubing 130 prior to manually boring the tube 130 or tubing 130 through the receptor compartment 120.

Figure 2B:
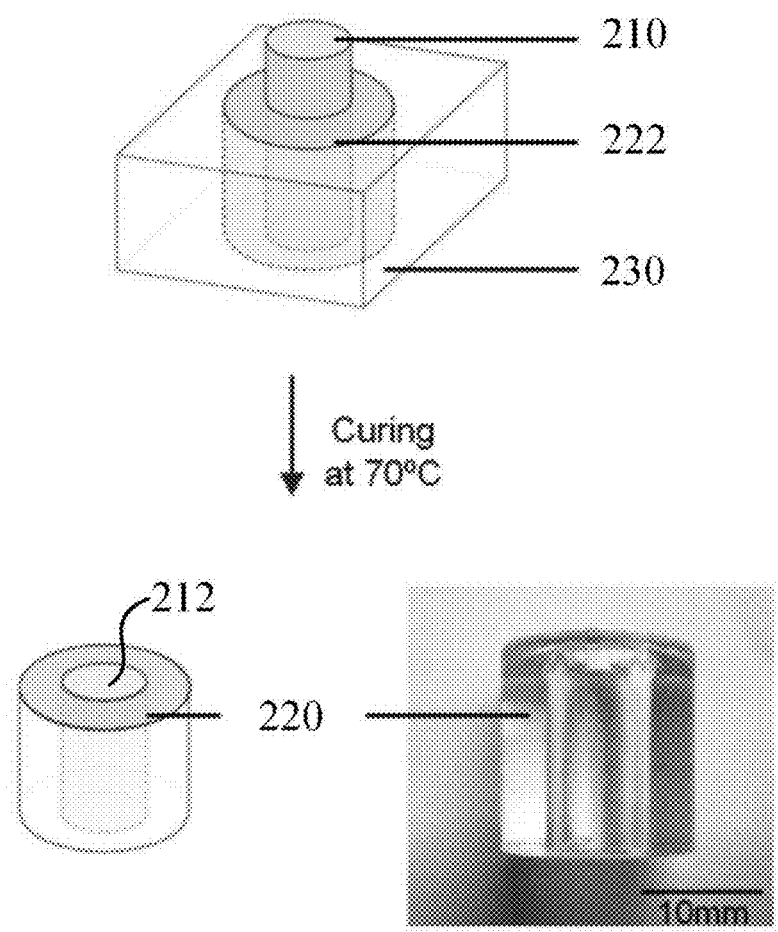
FIG. 2B is a schematic diagram of a fabrication process of a donor compartment in accordance with an embodiment of the present disclosure.
Figure 2C:
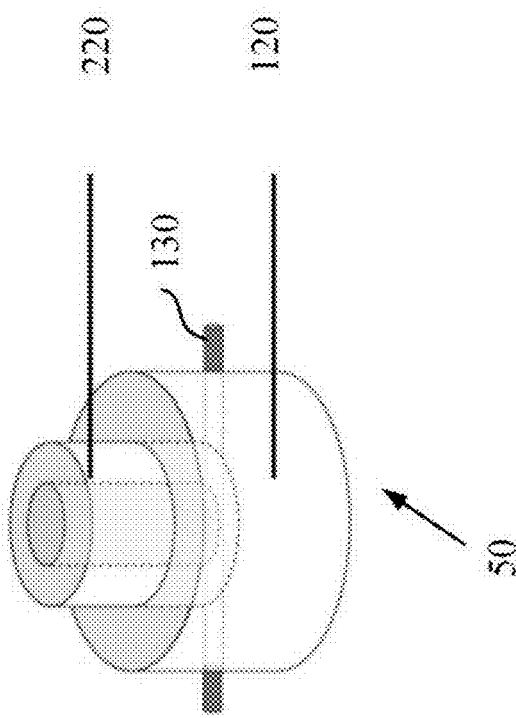
FIG. 2C is a schematic diagram of a full assembly of a fabricated diffusion cell in accordance with an embodiment of the present disclosure.

Referring to FIG. 2B, the donor compartment 220 having a length of 13 mm and a width of 16 mm was fabricated with a similar process in a single well of a 24-well plate 230. A 6 mm hollow lumen 212 was first created with a plastic or metal mold 210. The mold 210 was placed in the well of the 24-well plate 230 and PDMS was used to fill the space 222 between the external wall of the mold 210 and the 24-well plate 230 and was similarly cured at 70° C. for 2 hr. The plastic or metal mold 210 was removed to create a hollow cavity 212, to serve as the donor liquid compartment 212. In some embodiments, the size of the donor compartment 220 and the mold of the donor compartment 210 of the present disclosure can be modified as needed or per application requirements. In some embodiments, the shape of the donor compartment 220 and the mold of donor compartment 210 of the present disclosure can be cylindrical or cuboidal. Other shapes are also contemplated. In some embodiments, the mold of donor compartment 210 of the present disclosure can be made from other materials. In accordance with an embodiment of the present disclosure, the donor compartment 220 was designed to hold up to about 283 μl of drug solution with an area of about 0.283 cm². In some embodiments, the donor compartment 220 can hold a donor solution volume of about 70 μl to about 300 μl. In some embodiments, the area of the donor compartment 220 can be about 0.283 cm² to about 0.5 cm². FIG. 2C illustrates a diffusion cell 50 comprising a donor compartment 220, receptor compartment 120 and tube 130 or tubing 130.

1.3. Assembly and Operation of MFtC

Figure 2D:
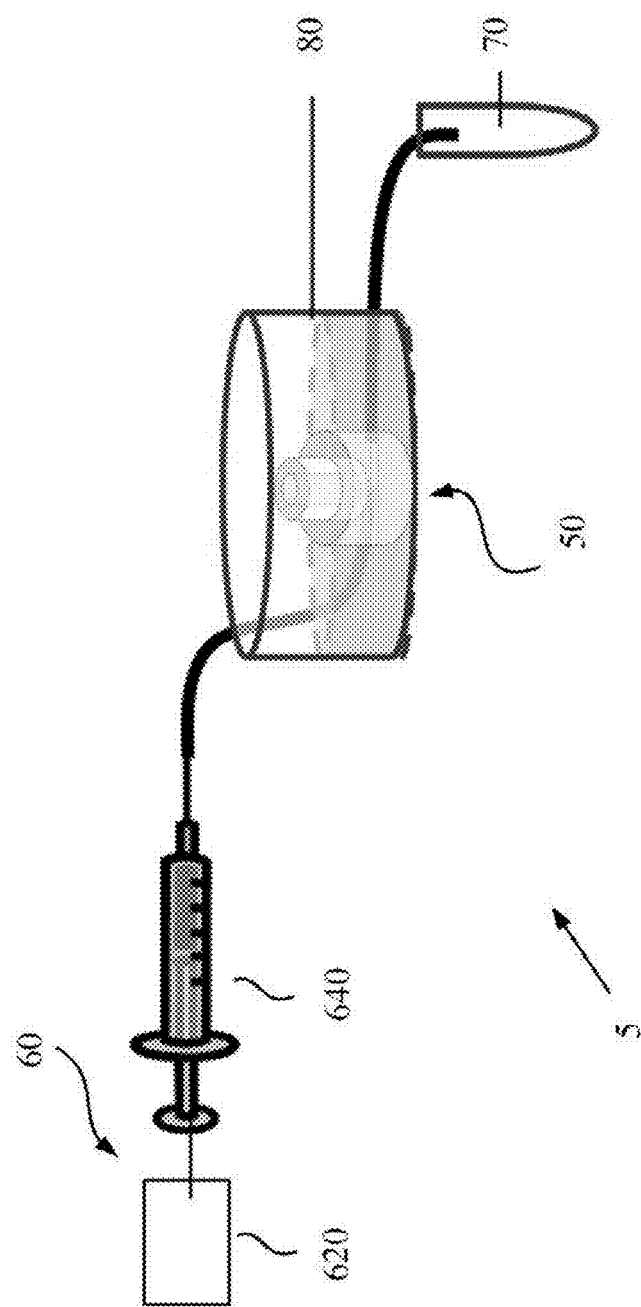
FIG. 2D is a schematic diagram of a full assembly of a miniaturized flow-through cell (MFtC) in accordance with an embodiment of the present disclosure.

Referring to FIG. 2D, the MFtC 5 was assembled by connecting the tube 130 or tubing 130 of the fabricated diffusion cell 50 to an infusion pump system 60 (Terufusion, UK), comprising a pump 620 or pumps 620 or pump assembly 620' together with a controllable receptor solution introducer 640 such as a syringe 640 or syringes 640 or syringe assembly 640' at one end and sampling tubes 70 or sampling container 70 at the other end. In some embodiments, other sampling containers 70 can be designed as needed or per application requirements. The fabricated diffusion cell 50 was then placed in a water bath 80 maintained at 37° C. using a hot plate. A drug solution/donor solution was placed in the donor liquid compartment 212 of the donor compartment 220. The flow rate of the receptor solution through the fabricated diffusion cell 50 was controlled by the infusion pump system 60. The infusion pump system 60 delivers the receptor solution from a controllable receptor solution introducer 640 such as a syringe 640 or syringes 640 or syringe assembly 640'. In embodiments of a MFtC of the present disclosure, the receptor solution was circulated using the infusion pump system 60.

Figure 3:
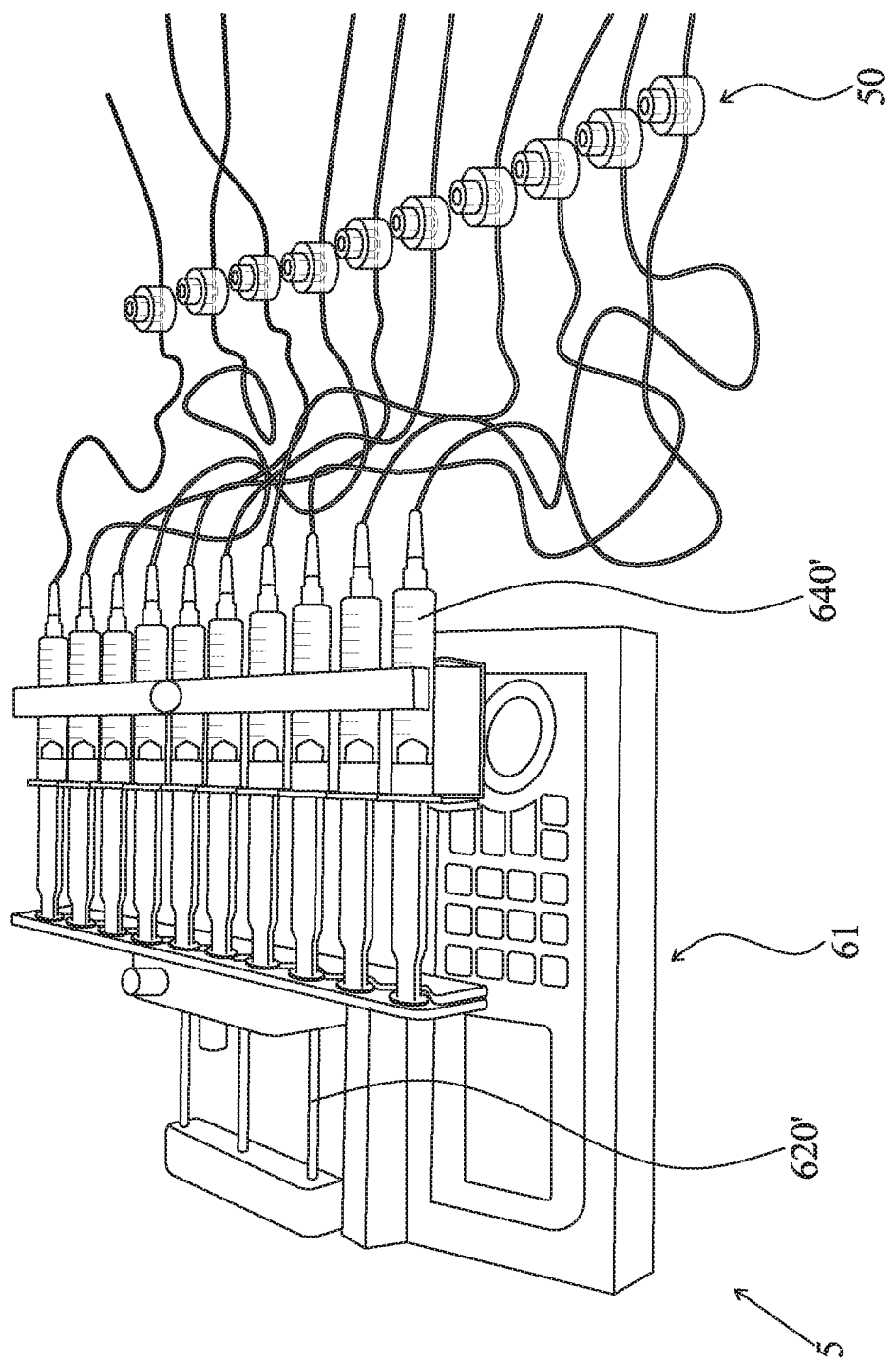
FIG. 3 illustrates a MFtC in accordance with an embodiment of the present disclosure, wherein the MFtC comprises ten diffusion cells, wherein each of the ten diffusion cells comprises a receptor compartment, wherein the ten diffusion cells are integrated with a ten-channel syringe pump system to deliver a receptor solution through each of the ten receptor compartments.

FIG. 3 illustrates a miniaturized flow-through cell (MFtC) 5 in accordance with an embodiment of the present disclosure, wherein the MFtC 5 comprises ten diffusion cells 50, wherein each of the ten diffusion cells 50 comprises a tube 130 or tubing 130, wherein the ten diffusion cells 50 are integrated with a ten-channel syringe pump system 61 or a ten-channel infusion pump system 61 to deliver a receptor solution contained in the syringe assembly 640' or controllable receptor solution introducer assembly 640' through each tube 130 or tubing 130 of the ten diffusion cells 50.

In some embodiment of the present disclosure, the MFtC 5 can comprise multiple diffusion cells 50 integrated with a multi syringe pump system.

In some embodiment of the present disclosure, the MFtC 5 can comprise two or more diffusion cells 50 integrated with a two-or-more-channel syringe pump system.

In some embodiment of the present disclosure, the MFtC 5 can comprise five or more diffusion cells 50 integrated with a five-or-more-channel syringe pump system.

In some embodiment of the present disclosure, the MFtC 5 can comprise ten or more diffusion cells 50 integrated with a ten-or-more-channel syringe pump system 61.

In some embodiment of the present disclosure, the MFtC 5 can comprise twenty or more diffusion cells 50 integrated with a twenty-or-more-channel syringe pump system.

In some embodiment of the present disclosure, the MFtC 5 can comprise a plurality of diffusion cells 50, wherein each of the diffusion cells 50 can be integrated with a syringe pump system 60 or an infusion pump system 60.

In some embodiments, the method of performing an assay using MFtC 5 can comprise: placing a membrane on top of the slit 132 or split 132 of the tube 130 or tubing 130. In some embodiments, the membrane can comprise a biological membrane and/or a synthetic membrane.

In some embodiments, the method of performing an assay using MFtC 5 can further comprise: placing the donor compartment 220 within the receptor compartment 120, wherein the donor compartment 220 sits on the membrane.

1.4. Validation of MFtC Against Horizontal Diffusion Cell

To evaluate the performance characteristics of the MFtC 5, permeation of model compounds (rhodamine B and mangostin) using a horizontal diffusion cell (TK-6H1, Shanghai Kai Kai Technology, China) and a MFtC 5 was compared.

Rat abdominal skins were obtained from the National University of Singapore Animal Centre and kept at −80° C. until use. Prior to the permeation studies, the skins were thawed and hair was completely removed with an electrical shaver and hair remover cream (Veet). Subcutaneous fat and connective tissues were also lightly trimmed off. All animal experiments were approved by Institutional Animal Care and Use Committee, National University of Singapore.

A 2.0 cm×2.0 cm piece of rat abdominal skin was mounted between the donor and receptor compartments of the horizontal diffusion cell, with the stratum corneum side facing the donor compartment. The effective diffusion area was 1.13 cm². Each donor cell contained 4.5 ml of each model compound in propylene glycol (PG) and the receptor cell contained the same volume of PBS. Mangostin was used at a concentration of 2.3 mg/ml and rhodamine B at concentrations of 1 mg/ml and 5 mg/ml. Both compartments were thermostated at 37° C. by means of a surrounding temperature controlled water jacket. In order to minimize evaporation, all cell openings were occluded with parafilm. The fluids in both compartments were maintained in a stirred state by a Teflon coated magnetic stirrer at a speed of 250±1.25 rpm. Samples (1 ml) were withdrawn from the receptor compartment for analysis at specific time intervals. Upon each sample withdrawal, the receptor compartment was immediately replaced by an equal volume of fresh solution. The experiments were performed in triplicates or more.

Figure 4:
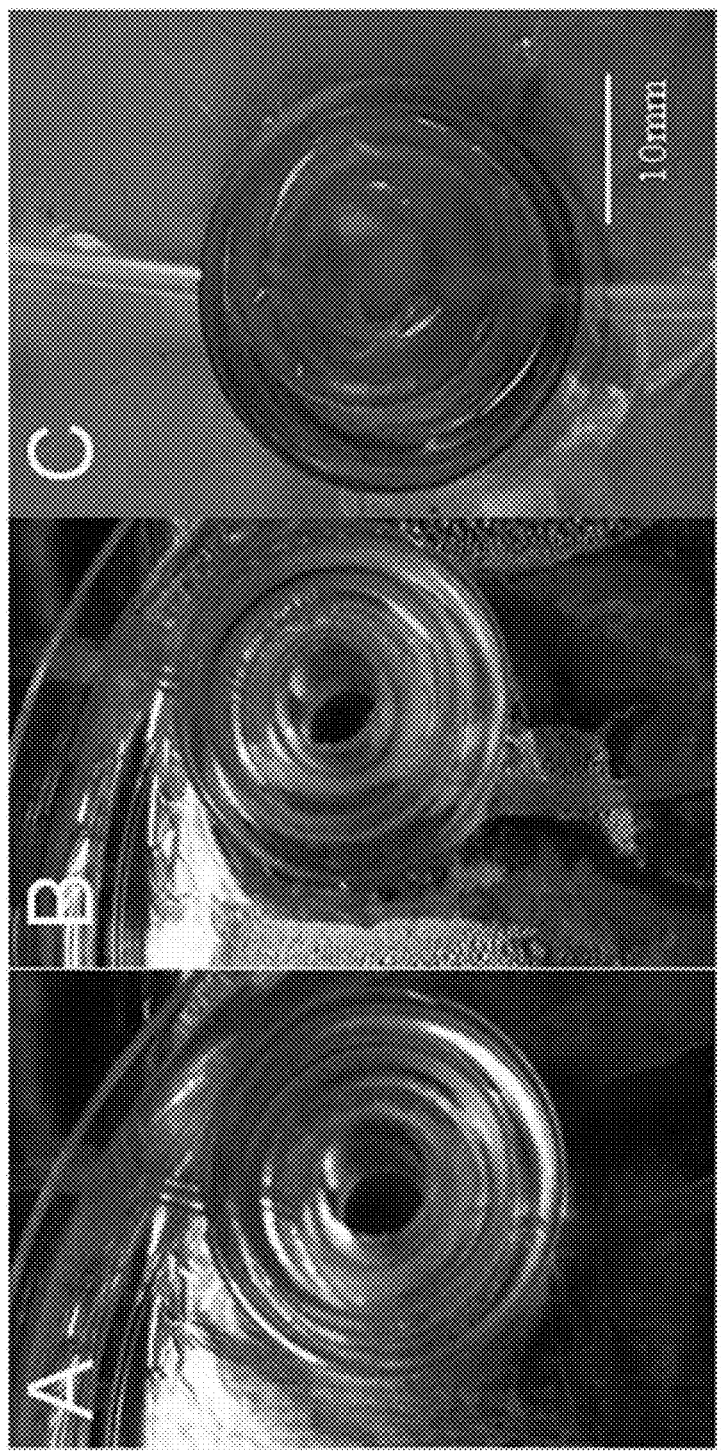
FIGS. 4A-4C are images of a MFtC in accordance with an embodiment of the present disclosure demonstrating the prevention of leakage due to the application of vacuum grease.

Similar conditions were used in the MFtC 5 or MFtC 5 setup. A 1.0 cm×1.0 cm piece of rat abdominal skin was mounted between the donor compartment 220 and the receptor compartment 120 with the stratum corneum side facing the donor compartment 220 of the MFtC 5. In some embodiments, the area and shape of the skin/membrane of the present disclosure can be modified as needed or per application requirements. A sealant or sealing substance or material such as high vacuum grease (Dow Corning, USA) was applied to the donor compartment 220 on the unexposed stratum corneum side, in contact with the receptor compartment 120, to minimize leakage from the donor compartment 220. Other sealants, sealing substances, or high vacuum grease for minimizing leakage from the donor compartment 220 can be selected as needed or per application requirements. As shown in FIG. 4, the application of grease prevented the leakage of donor solution, even at the end of a 48 hour study. On the other hand, leakage of the donor solution could be observed when no grease was applied.

In an embodiment of the present disclosure, the effective diffusion area was 0.283 cm$^2$. In some embodiments, the effective diffusion area can be about 0.283 cm$^2$ to about 0.5 cm$^2$. In an embodiment of the present disclosure, 70 μl of the donor solution was added into the donor compartment 220. In some embodiments, the volume of the donor solution added to the donor compartment 220 can be about 70 μl to about 300 μl. In an embodiment of the present disclosure, the receptor fluid or receptor solution comprised degassed PBS solution. In some embodiments, the receptor solution of the present disclosure can comprise other solutions such as water, buffers, extracellular fluid, lung lining fluid, gastric fluid, and/or cerebrospinal fluid.

In an embodiment of the present disclosure, the flow rate of receptor solution through each diffusion cell 50 can be controlled by an infusion pump system 60, wherein the flow rate can be about 0.20 ml/hr. In some embodiments, the flow rate of receptor solution through each diffusion cell 50 can be reduced or increased to a flow rate of about 0.828 μl/hr to about 1270 ml/hr as needed or per application requirements.

An embodiment of a MFtC 5 of the present disclosure was placed in a temperature controlling system such as a water bath 80 maintained at 37° C. using a hot plate to control the temperature. In some embodiments, the temperature can be adjusted as needed or per application requirements. In order to minimize evaporation, the donor compartment 220 and sampling container(s) 70 such as a sampling microfuge tube(s) 70 were occluded with parafilm. The sampling container(s) 70 such as a sampling tube(s) 70 was collected at specific time intervals and replaced by a sampling container(s) 70 such as an empty sampling tube(s) 70 for subsequent collections. The experiments were performed in triplicates or more. In some embodiments, the method of collecting the sample can be modified as needed or per application requirements.

Skin samples from the same rat were used for comparisons between the horizontal diffusion cell and a MFtC 5 to minimise inter-animal variability. All experiments were performed at least three times. The samples were collected at the same time intervals and stored at 4° C. until analysis. During analysis, samples were first centrifuged at 13,000 rpm (Sorvall Biofuge Pico, UK) for 5 min. The supernatant was obtained and analyzed according to their respective assay methods as reported below.

Concentration of rhodamine B was determined by fluorescence spectroscopy with a microplate reader (Tecan, Switzerland) at an excitation wavelength ($\lambda_{ex}$)=554 nm and an emission wavelength ($\lambda_{em}$)=586 nm at ambient temperature. All samples were protected from light to prevent possible light quenching of fluorescence during the assay.

Mangostin concentration was determined with a reversed phase HPLC (Hitachi, Japan) using a $C_{18}$ column (5 μm, 4.6 mm×250 mm; ODS Hypersil, Thermo Scientific) maintained at ambient temperature. The mobile phase comprised of methanol and ultrapure water (90:10, v/v) delivered at a flow rate of 1 ml/min. The UV detector (L-2400, Hitachi, Japan) was operated at a λ=320 nm. Under these conditions, the mangostin peak appeared at a retention time of 6.8 min.

A comparison of the change in the properties of a piece of skin when applied to a MFtC 5 and a horizontal diffusion cell for a particular period of time was performed by histological examination of the skin. For this purpose, defatted rat skin was clamped in the diffusion cells of the MFtC 5 and horizontal diffusion cell in a manner as described above. PG was applied to hollow cavity 212 of the donor side or donor compartment 220. The receptor solution was comprised of PBS. Histological examination of the skin applied to the MFtC 5 and the horizontal diffusion cell was carried out at 0, 24 and 48 hours post application by cutting the skin longitudinally into 20 μm sections using a microcryostat (Leica, Germany). Subsequently the sections were fixed in absolute ethanol and stained with hematoxylin and eosin and imaged using a Nikon AZ100 (Nikon, Japan) microscope.

1.5. Endoxifen Fluorescence Assay

A fluorescence assay for endoxifen was established whereby endoxifen was converted to highly fluorescent phenanthrene derivatives following exposure to ultraviolet (UV) irradiation. A UV transilluminator (Bio Rad, USA) at λ=302 nm and an intensity of 866 μW/cm$^2$ was used for the conversion of endoxifen to its phenanthrene derivatives. The fluorescence emitted from the phenanthrene derivatives of endoxifen after various durations of UV exposure was determined with a microplate reader at a $\lambda_{ex}$=260 nm and a $\lambda_{em}$=380 nm. Fluorescence measurements from non-UV exposed samples served as a control. The optimum duration of UV irradiation was determined with a 10 μg/ml solution of endoxifen. For all subsequent experiments, this duration of UV irradiation was fixed at the optimal time.

The linearity and sensitivity of the assay were determined by spiking endoxifen in PBS at Eleven concentrations (0.78-25.00 μg/ml). The fluorescence, obtained post UV irradiation, was plotted against endoxifen concentrations. Linear regression was performed to obtain the slope and intercept. The limit of detection (LOD) and limit of quantification (LOQ) were set as three and ten times the standard deviation of the blank respectively.

The intra-day accuracy and precision of the assay method were determined by spiking receptor solution collected from a permeation study with PG as the donor solution with four concentrations (1.56-12.50 μg/ml) of endoxifen. Aliquots of these samples were analyzed on three occasions on the same day. Triplicates were prepared for each analysis.

1.6. Endoxifen Permeation Studies

The validated MFtC 5 mounted with rat abdominal skin was employed to determine the permeation profile of endoxifen. Donor solutions comprised of endoxifen (2 mg/ml) in PG with and without permeation enhancers (PEs) namely limonene, myristyl lactate and oleic acid at 0.5% (w/v) were prepared. All solutions were sonicated for 3 min to ensure dissolution of endoxifen and PEs. Each donor compartment 220 was filled with 200 μl of donor solution. Endoxifen was allowed to permeate through the rat abdominal skin over 48 hr. The experiments were performed in triplicates. Samples of permeated solutions were collected at specific time intervals and stored at −20° C. until analysis. The flux at steady state ($J_{ss}$) and lag time were obtained from the cumulative plots. The effect of the PEs on the flux was evaluated by calculating the enhancement index (EI).

1.7. Statistical Analysis

Independent sample t-test (IBM SPSS PASW Statistics 18) was used to compare the permeation parameters obtained from experiments involving horizontal diffusion cell and MFtC 5. For endoxifen permeation experiments, one-way analysis of variance (ANOVA) with Scheffe post hoc test was used for the comparison of the permeation parameters of endoxifen with or without the different PEs. For all tests, p<0.05 was considered significant.

2. Results 2.1. Validation of MFtC Against Horizontal Diffusion Cell

As shown in Table 1, for the receptor liquid, an average flow rate of 0.18±0.01 ml/hr was measured. The choice of low flow rate was selected to achieve adequate drug to be present in the samples for detection and quantification. This is particularly important in the case of low flux. It was reported that flow rate of the receptor solution does not affect the numerical value of the flux of drug but the time to achieve steady state instead. Therefore, any small fluctuations in the flow rate would not influence the flux significantly.

TABLE 1

Flow rate (ml/hr) of the receptor solutions (mean ± SD), N = 9.

| Flow rate (ml/hr) | | | Accuracy | RSD |
|---|---|---|---|---|
| Run 1 | Run 2 | Mean | (%) | (%) |
| 0.17 ± 0.01 | 0.19 ± 0.01 | 0.18 ± 0.01 | 88.50 | 7.94 |

Figure 5:
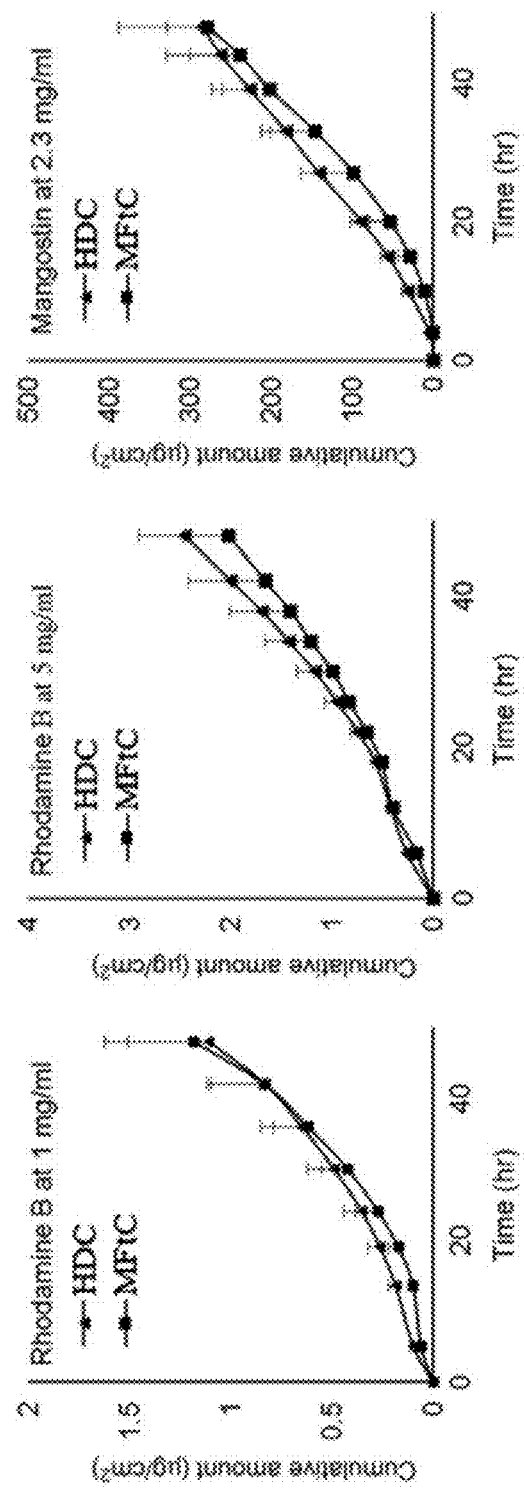
FIG. 5 illustrates the cumulative amount of rhodamine B at 1 mg/ml, rhodamine B at 5 mg/ml and mangostin at 2.3 mg/ml that permeates through rat abdominal skin over time using a known horizontal diffusion cell (HDC) and an embodiment of a MFtC of the present disclosure, wherein each point represents a mean±SD of the cumulative amount.

The different nature of the two model substances (rhodamine B and mangostin) and varied concentrations were chosen to ensure the reproducibility of permeation parameters in the presence of different test substances. No significant difference in $J_{ss}$ (p>0.05) was found between the horizontal diffusion cell and the MFtC 5 for the three different donor solutions (FIG. 5 and Table 2). While the design of the MFtC 5 varies significantly from that of the horizontal diffusion cell, the results obtained confirmed that permeation profiles from both the set-ups were comparable, thereby confirming that the MFtC 5 fabricated is a suitable platform for reproducible results for scaled-down permeation studies.

TABLE 2

Comparison of lag time and fluxes between an HDC and a MFtC 5 across rat abdominal skin using rhodamine B at 1 mg/ml, rhodamine B at 5 mg/ml and mangostin at 2.3 mg/ml, wherein N denotes number of replicates and error bars denote SD between replicates, wherein flux comparisons between the setups showed no statistical difference.

| | Rhodamine B (1 mg/ml) | | | Rhodamine B (5 mg/ml) | | | Mangostin (2.3 mg/ml) | | |
|---|---|---|---|---|---|---|---|---|---|
| | N | Lag time (hr) | Flux (μg/cm²/hr) | N | Lag time (hr) | Flux (μg/cm²/hr) | N | Lag time (hr) | Flux (μg/cm²/hr) |
| HDC | 5 | 17.7 ± 3.47 | 0.04 ± 0.03 | 4 | 11.4 ± 3.31 | 0.07 ± 0.01 | 5 | 7.19 ± 0.47 | 7.06 ± 1.06 |
| MFtC | 3 | 22.1 ± 4.07 | 0.05 ± 0.02 | 5 | 8.35 ± 4.75 | 0.05 ± 0.02 | 7 | 14.5 ± 2.71 | 8.34 ± 3.40 |

Figure 6:
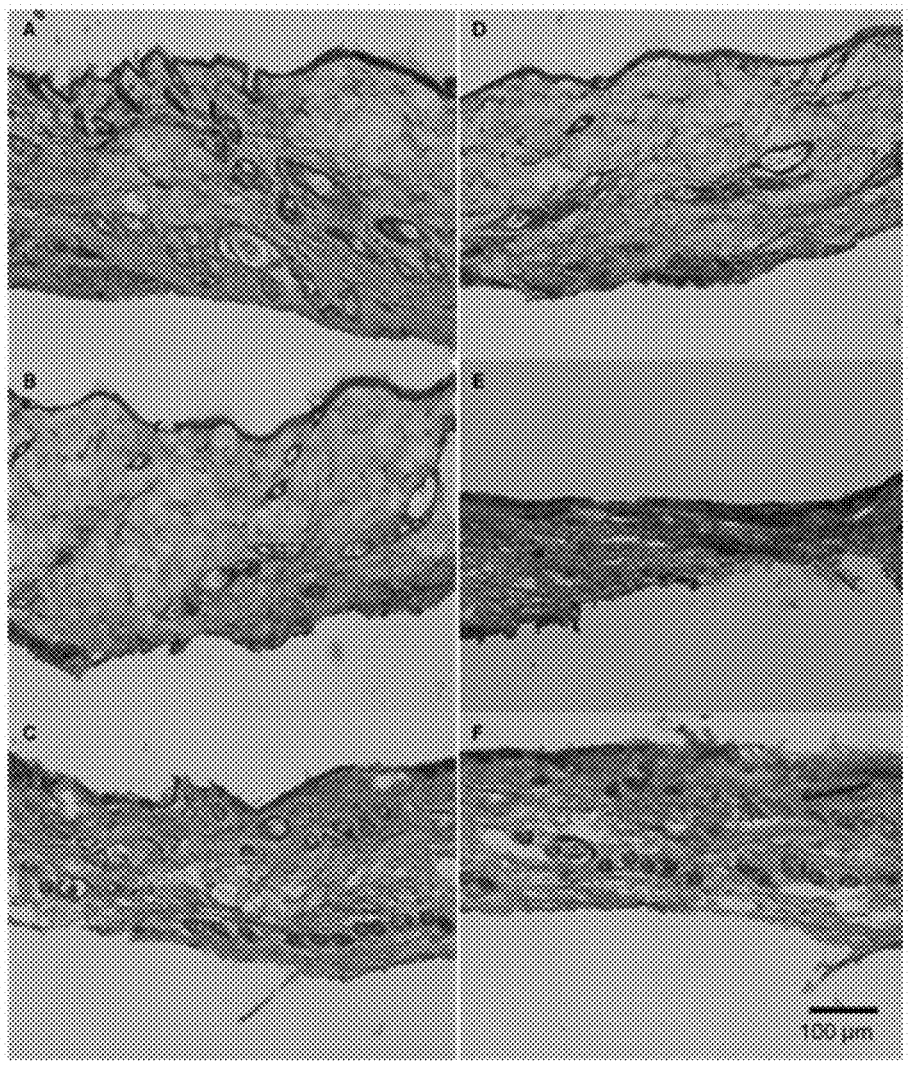
FIG. 6A is a histological image of skin mounted on a MFtC at 0 hours.
FIG. 6B is a histological image of the skin mounted on a MFtC at 24 hours.
FIG. 6C is a histological image of the skin mounted on the MFtC at 48 hours.
FIG. 6D is a histological image of skin mounted on a horizontal diffusion cell at 0 hours.
FIG. 6E is a histological image of the skin mounted on the horizontal diffusion cell at 24 hours.
FIG. 6F is a histological image of the skin mounted on the horizontal diffusion cell at 48 hours. The images demonstrate that no apparent damage to the skin was caused by the MFtC and the skin mounted on the MFtC exhibited similar properties as compared to the skin mounted on a horizontal diffusion cell.

Histological examination of the skin from both diffusion cells revealed that there were no apparent changes in the skin structure over a period of 48 hours (FIG. 6). The structure of stratum corneum obliterated minimally, particularly for the first 24 hours of the permeation study. However, shrinkage of the skin thickness was observed in both the diffusion set-ups. This can be attributed to the continuous shredding of the skin as it is in contact with the donor and receptor fluids. Also, the excised skin loses its inherent water content, leading to transepidermal water loss and the resultant shrinkage.

2.2. Endoxifen Fluorescence Assay

Figure 7:
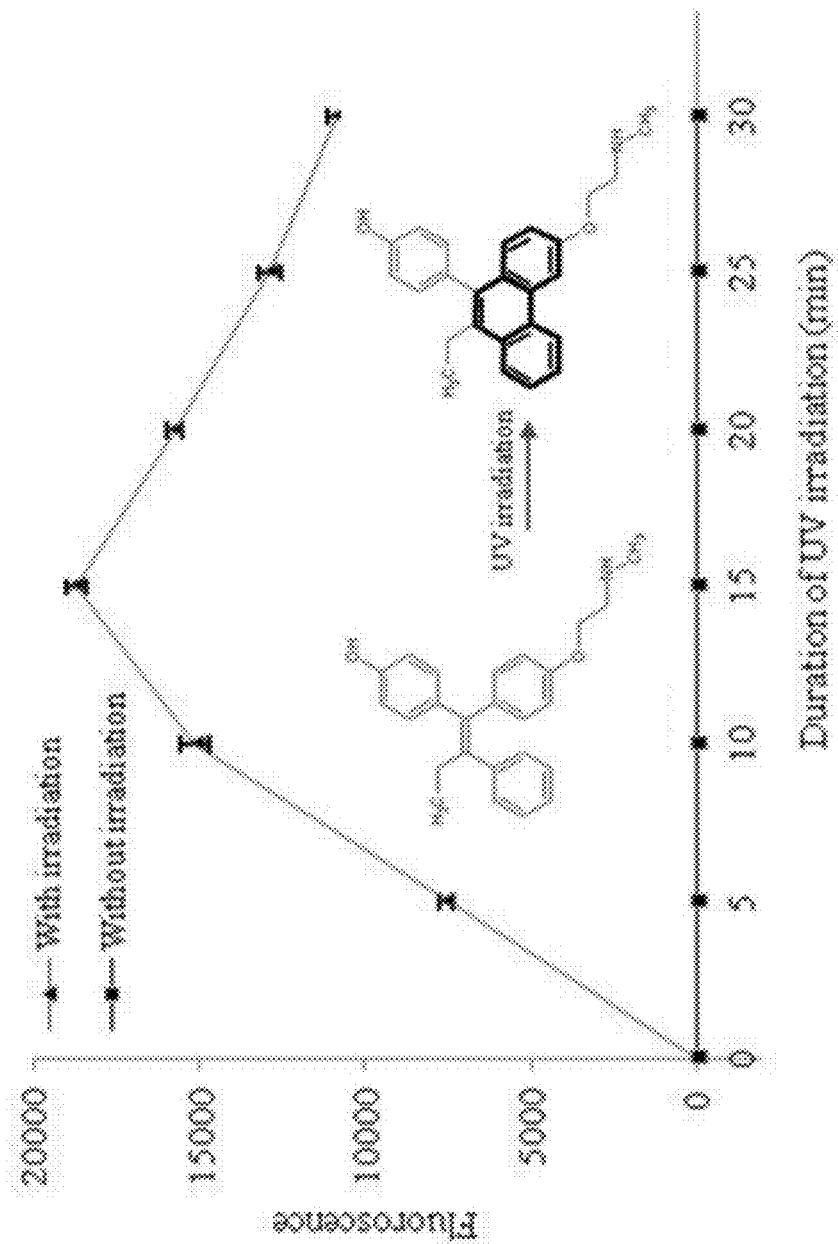
FIG. 7 is a plot of the fluorescence emitted for endoxifen (ENX) in ultrapure water (10 µg/ml) against the duration of UV irradiation wherein each point represents a mean±SD (N=3), wherein the inset of FIG. 7 illustrates the photocyclization of ENX into a product with a phenanthrene core.

Endoxifen, without irradiation, emits minimal fluorescence. Following UV irradiation, the phenanthrene derivatives of endoxifen emitted fluorescence, which is dependent on the amount of UV exposure. As shown in FIG. 7, the optimum duration of UV irradiation of 15 min, which corresponds to maximum fluorescence value, was used for all subsequent experiments.

In order to ensure accurate quantification of endoxifen, the linearity and sensitivity of the fluorescence based assay was determined using calibration experiments. The regression curve was obtained and the limits were:

Range: 0.78-3.13 μg/ml, A=(510.7±90.7) [endoxifen]−(422.4±93.4), $r^2$=0.97

Range: 3.13-25.00 μg/ml, A=(1226.5±38.8) [endoxifen]−(2663.4±149.1), $r^2$=0.98.

N=4, LOD=0.31 μg/ml, LOQ=0.78 μg/ml, where A is in arbitrary units and the concentration is in μg/ml.

As shown in Table 3, accuracy and precision were assessed using four concentrations, i.e., 1.56 μg/ml, 3.13 μg/ml, 6.25 μg/ml and 12.50 μg/ml. An accuracy of +2.05%, +18.86%, +11.41% and +19.06% with an inter-day CV of 2.99%, 5.21%, 1.68% and 4.82% was respectively observed.

TABLE 3

Intra-day precision and accuracy. N = 3.

| Actual concentration (μg/ml) | Recovered concentration (mean ± SD) (μg/ml) | Accuracy (%) | Intra-day CV (%) |
|---|---|---|---|
| 12.50 | 14.88 ± 0.72 | +19.06 | 4.82 |
| 6.25 | 6.96 ± 0.12 | +11.41 | 1.68 |
| 3.13 | 3.71 ± 0.19 | +18.86 | 5.21 |
| 1.56 | 1.59 ± 0.04 | +2.05 | 2.99 |

2.3. Endoxifen Permeation Studies

Figure 8:
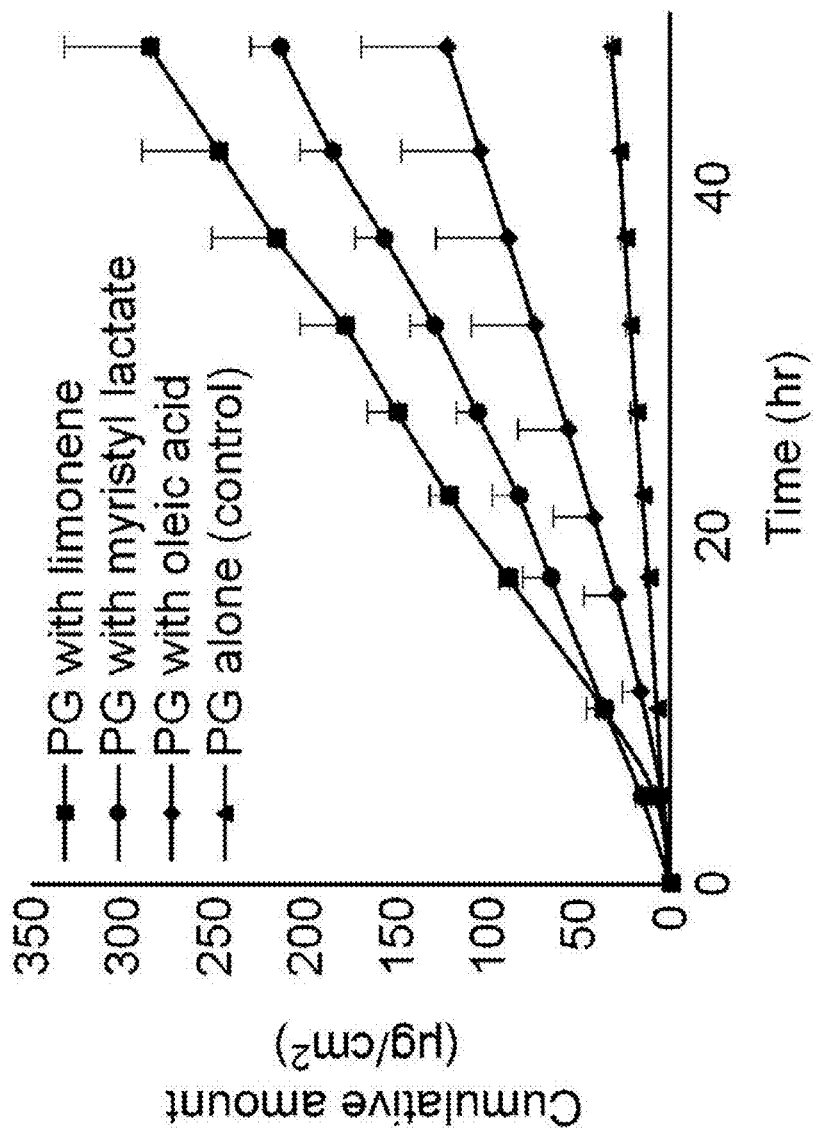
FIG. 8 illustrates the cumulative amount of ENX permeated through the rat abdominal skin with an area of 0.283 $cm^2$ over time with or without permeation enhancers (PEs) using a MFtC, wherein the ENX donor concentration is equal to 2 mg/ml in propylene glycol (PG) with or without PEs (namely, limonene, myristyl lactate and oleic acid at 0.5% w/v), and each point represents a mean±SD.

Cumulative permeation plots and permeation parameters of endoxifen in PG with and without PEs are shown in FIG. 8 and Table 4. All PEs significantly increased (p<0.05) the endoxifen flux in comparison with the PG alone. Endoxifen in PG with 0.5% w/v oleic acid, myristyl lactate and limonene achieved an EI of 6.26, 8.17 and 9.99 respectively, when compared to endoxifen in PG alone. The highest $J_{ss}$ was achieved using limonene as a PE, with an EI of about ten times more than PG alone. Lag time of permeation for endoxifen in PG alone was however lower than those achieved with the use of PEs.

TABLE 4

Permeation parameters of ENX in various donor solutions. Data was expressed as mean ± SD. PE concentration = 0.5% (w/v). (N = 3). Enhancement index (EI) = $J_{ss}$ (with enhancer)/$J_{ss}$ (without enhancer).

| Donor solution | Lag time (h) | Flux (µg/cm$^2$/hr) | EI |
|---|---|---|---|
| PG alone (control) | 1.03 ± 1.40 | 0.65 ± 0.01 | — |
| PG with oleic acid | 7.58 ± 4.04 | 4.09 ± 1.07* | 6.26 |
| PG with myristyl lactate | 7.62 ± 2.18 | 5.33 ± 0.13* | 8.17 |
| PG with limonene | 3.75 ± 2.37 | 6.52 ± 1.41* | 9.99 |

*p < 0.05 compared to control.

3. Discussion

3.1. Choice of PDMS for the Fabrication of MFtC

PDMS was selected for the fabrication of the MFtC 5 because of its advantageous properties. Firstly, the total cost of such a device was reduced substantially, thereby making such a setup readily affordable. The fabrication process is simple and can be easily adapted by individual research labs or other users to customize their diffusion cells as per their specific requirements. A single diffusion cell 50 made of PDMS approximately costs 1 USD (material cost) as compared to commercial equivalent that costs around 440 USD.

Secondly, the rheological properties of PDMS allow shaping of any desired design due to its flowability into any pre-formed mold. Owing to the flexible nature of PDMS, miniaturization of the whole assembly could be made possible. As shown in Table 5, the MFtC 5 had significantly lower donor area, donor and receptor volumes as compared to the currently known commercial flow-through cells. The low receptor flow rate of 0.20 ml/hr is in accordance with the general rule that flow rate should be at least ten times the receptor volume (10 µl).

TABLE 5

Comparison between the MFtC 5 and commercial flow-through cells.

| Mechanical elements | MFtC | Commercial |
|---|---|---|
| Donor area | 0.283 cm$^2$ | 0.785 cm$^2$ |
| Donor volume | 70-200 µl | 100-1000 µl |
| Receptor volume | 10 µl | 230-855 µl |

In addition, the optical clarity of PDMS allows a clear view of the area below the skin. This in turn facilitates the ascertainment of the absence of air bubbles which is especially important as these air bubbles can adversely affect the accuracy of permeation results. Lastly, PDMS being an inert material allows for the prolonged shelf life of the diffusion cell 50 and makes the diffusion cell 50 reusable.

Moreover, it has been reported the adsorption of PDMS is comparable to glass, especially for hydrophilic compounds while it is four times higher than glass for hydrophobic compounds. While most of the compounds used in the present disclosure were relatively hydrophobic, significant loss of drugs due to adsorption was not observed. If needed, the surface of PDMS can be modified physically or chemically, to reduce the adsorption of hydrophobic drug molecules.

In accordance with an embodiment of the present disclosure, a diffusion cell 50 made of PDMS can be made reusable by washing with acetone and isopropanol. In some embodiments, the cleaning and/or washing procedures can be modified as needed or per application requirements.

In some embodiments, the MFtC 5 can be made of photocurable perfluoropolyethers. In some embodiments, the MFtC 5 including the donor compartment 220 and the receptor compartment 120 can be made from materials that are moldable, materials having similar properties to PDMS, materials having optical clarity, materials that are flexible, materials that are inert, and/or materials that exhibit low adsorption of compounds (i.e., drug compounds, active agents, cosmetic compounds, etc).

3.2. Validation of MFtC Against Horizontal Diffusion Cell

While validating the newly fabricated MFtC 5 against the established permeation equipment, horizontal diffusion cells, two factors were considered, namely, the varied concentrations and the chemical nature or log P of the compounds. First, two different concentrations of rhodamine B were validated to investigate the validity of flux at low and high concentrations of the donor solution. Rhodamine B is a fluorescent molecule, with a suitable log P (2.43) and molecular weight (479.02) for skin permeation testing. Its pink color aids in easy detection of leakage of the donor solution as shown in FIG. 4. It was observed that the flux achieved was comparable for both the concentrations between MFtC 5 and the horizontal diffusion cells. Second, as shown in FIG. 1, the permeation parameters or permeation profiles of rhodamine B and mangostin were compared in terms of molecular structures and molecular weights. Mangostin is a molecule similar to rhodamine B but mangostin with a higher log P value (log P=6.64) than rhodamine B (log P=2.43). Log P is an important parameter to consider for skin permeation, as it will affect the partition of the drug inside stratum corneum and viable layers of epidermis. Mangostin extensively permeates the skin, possibly due to its higher log P values. It was observed that the permeation parameters of MFtC 5 and the horizontal diffusion cell were in close correlation to each other, signifying the validity of the MFtC 5 of the present disclosure.

Figure 9:
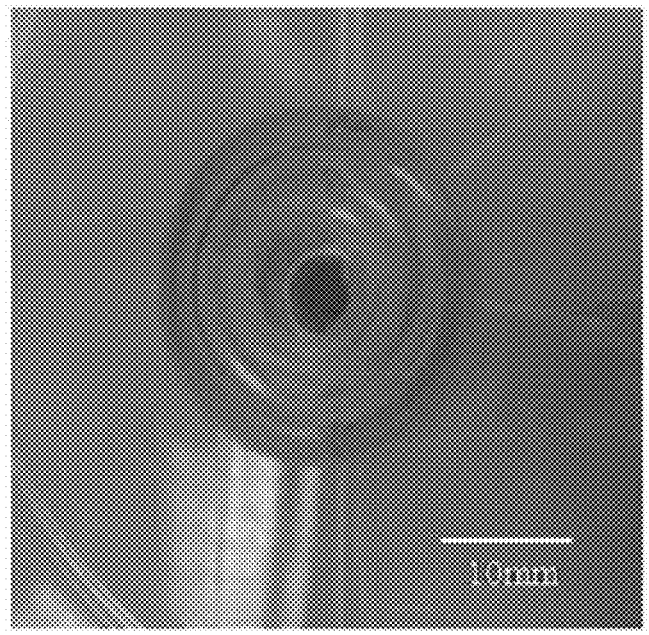
FIG. 9 illustrates a MFtC with pig skin showing the ability of the MFtC to be used with thicker skin samples without any leakage problem.

The MFtC 5 was also adaptable for thicker skin samples, such as those from pig cadaver, which closely resemble human skin. Referring to FIG. 9, pig skin was supported on the MFtC 5 with the application of vacuum grease and no leakage was detected from the donor compartment 220 when a rhodamine B solution in PG was applied.

3.3. Endoxifen Permeation Studies

To achieve a plasma concentration of endoxifen that is comparable to those achieved on administration of an oral daily dose of 2.0-4.0 mg, an ideal flux of 2.0-4.0 µg/cm$^2$/hr, assuming an application area of 40 cm$^2$ would be required from endoxifen transdermal drug delivery system. The reported transdermal endoxifen study was not able to achieve this flux. The highest flux reported was 0.22 µg/cm$^2$/hr for endoxifen dissolved in 60% (v/v) ethanol-phosphate buffer with 0.5% (w/v) oleic acid.

In the search of a suitable vehicle and suitable PEs for endoxifen in transdermal drug delivery system, three different permeation enhancers were used. It has been reported that high skin flux of tamoxifen can be achieved by using limonene as a PE with PG as the vehicle. Because of the molecular structural similarities between tamoxifen and endoxifen, endoxifen was incorporated in PG while limonene was selected as one of the PEs in an embodiment of the present disclosure. In addition to limonene, oleic acid and myristyl lactate were also selected as PEs in embodiments of the present disclosure. In some embodiments, the permeation enhancer (PE) can be selected based on application requirements. In some embodiments, the vehicle can be selected based on application requirements.

As shown in Table 4, it was found that oleic acid, myristyl lactate and limonene in PG enhanced the permeation of endoxifen by 6.26, 8.17 and 9.99 folds respectively as compared to PG alone. Oleic acid has been reported to increase drug transport by coexisting as pools in the stratum corneum lipids structure. Myristyl lactate may act by disrupting ceramide-cholesterol or cholesterol-cholesterol interaction and increase permeation of endoxifen. As myristyl lactate (log P=6.08) has a shorter carbon chain than oleic acid (log P=7.42), the higher flux achieved by myristyl lactate can be explained by lower partitioning of drugs into stratum corneum as compared to oleic acid.

Results showed that limonene delivered the highest flux among the three PEs tested. Limonene belongs to the class of terpenes which are constituents of essential oils. Their ability to enhance drug flux could have been attributed to partial extraction of stratum corneum lipids, phase separation within the SC lipid lamellae and limonene-PG synergy.

Besides, the results using oleic acid as a PE in PG has shown significantly better endoxifen delivery with a $J_{ss}$ of 4.09±1.07 μg/cm$^2$/hr compared with the $J_{ss}$ of 0.22 μg/cm$^2$/hr as reported by using ethanol-phosphate buffer as the vehicle. A plausible explanation for this observation is the different effects of various vehicles on the skin. It has been reported that PG can affect the transdermal permeability by altering thermodynamic activity of drug and/or barrier nature of skin. Moreover, it is also known that activity of PEs can be significantly increased when applied in combination with PG. Overall, all three PEs chosen in the present disclosure were able to achieve higher flux than control. The best one was limonene, which attained a flux of 6.52 μg/cm$^2$/hr through rat skin, which can be translated to a flux of 2.17 μg/cm$^2$/hr through human skin. Therefore, the target flux of 2.0-4.0 μg/cm$^2$/hr through human skin can be achieved with this limonene formulation.

In some embodiments, the boring of a tube(s) 130 or a tubing(s) 130 through the receptor compartment 120 of the MFtC 5 of the present disclosure can be carried out manually. For example, the boring can be carried out manually using a cutter, clipper, or a specifically sized die bore.

In some embodiments, the method of manufacturing the diffusion cell 50 and MFtC 5 of the present disclosure can be made more streamlined. In some embodiments, the diffusion cell 50 and MFtC 5 of the present disclosure can be manufactured on an industrial scale. In some embodiments, the diffusion cell 50 and MFtC 5 of the present disclosure can be manufactured on a small scale.

In some embodiments, a MFtC 5 of the present disclosure can be a fully functional automated integrated MFtC 5.

Firstly, in some embodiments, 3D prototyping can be used to create receptor compartment molds for inserting a tube(s) 130 or tubing(s) 130. This would enable more uniformity in the design and aid in integrating the receptor compartment with the syringe pump system 60 and autosampler. Moreover, in some embodiments, a heating block can be used to provide a platform for MFtC 5 to obviate the need for immersing the diffusion cells 50 in a water bath 80. In some embodiments, a multi syringe pump system or multi-channel pump system can be used instead of a system comprising a plurality of syringes wherein each syringe is integrated with a separate pump. The multi syringe pump system/multi-channel pump system can be used to ensure variability in flow rate is minimized. The multi syringe pump system/multi-channel pump system can reduce the variation in pumping pressure between various pumps which lead to different flow rates.

In some embodiments, an autosampler can be integrated at the receiving end of the tube 130 or tubing 130 to provide for 24 hour automated sample collection. The design of the MFtC 5 can be modified to include features such as a pump control and/or service flask as needed or per application requirements. One or more of these enhancements can be used to make embodiments of the MFtC 5 of the present disclosure that are readily usable and marketable. In addition, the design of MFtC 5 can be modulated to suit other modes of transdermal administration, such as microneedles, iontophoresis, etc. This may require some tailoring with respect to the design of the donor compartment 220 and receptor compartment 120 to fit in the drug delivery system.

Some embodiments can exclude or omit additional elements for mixing or stirring purposes (e.g., a stirrer or a magnetic stirrer) as the action of the infusion pump system 60 can be sufficient in and of itself to circulate the receptor solution, mix the receptor solution and the permeate donor solution, and carry the permeate donor solution to the sampling container.

4. Advantages and Practical Application

The currently available permeation apparatus, due to their inherent design, require large amount of donor solutions (100-1000 μl). The flow thorough cells also have a high receptor flow rate, which dilutes the permeated drug, making it difficult to be analysed by conventional analytical procedures. This is critical as most drugs have low permeability across. Moreover these commercial versions come at a premium cost, which many scientists cannot afford. The present disclosure can solve each one of these issues. MFtC 5 can greatly reduce the amount of drug donor solution (70 to 200 μl) for skin permeation studies. Thus, this can allow the study of permeation properties using low amount of the drug, especially important for costly drugs. In addition, MFtC 5 can greatly reduce the amount of membrane (0.283 cm$^2$) for skin permeation studies, compared with some other cells, e.g. commercial cells that need skin with an area of 0.785 cm$^2$, for skin permeation studies. Together with this, the integration of the diffusion cell 50 to a syringe pump system 60/an infusion pump system 60 or a multi syringe pump system utilizing a low receptor flow rate can ensure that the permeated drug is not excessively diluted and hence does not pose a challenge in subsequent analysis.

Even at low donor and receptor volumes, the permeation characteristics of the MFtC 5 were observed to be similar to the horizontal diffusion cells. The histological sectioning of the skin from both the cells showed similar properties after the drug permeation study.

Besides, the affordability (e.g., material cost of about 1 USD), the ease of fabrication and versatility in design manipulation of the diffusion cells 50 make the use of the diffusion cells 50 of the present disclosure enticing for one to employ.

In some embodiments of the present disclosure, a MFtC 5 with a disposable diffusion cell(s) 50 can be developed for permeation testing to overcome the problem of contamination. Drug permeation studies of expensive drugs like biotherapeutics including peptides, proteins, vaccines, etc. can be made possible with the novel, simple and cost effective method of the present disclosure.

5. Conclusion

A miniaturized flow-through cell (MFtC) 5 in accordance with an embodiment of the present disclosure can utilize a small amount of donor solution (i.e., 70-200 µl) and a small amount and/or area of membrane (i.e., 0.283 cm$^2$) for skin permeation studies. The MFtC 5 had no damaging effect on the skin as compared to the established models like horizontal diffusion cell. A novel fluorescent spectroscopic method was also developed to quantify endoxifen in a fast and convenient manner. Permeation studies of endoxifen attained the targeted flux of 2.0-4.0 µg/cm$^2$/hr. The MFtC 5 is demonstrated to be useful for investigative drugs with limited supply during the pre-formulation studies.

While various aspects and embodiments have been disclosed herein, it will be apparent that various other modifications and adaptations of the invention will be apparent to the person skilled in the art after reading the foregoing disclosure without departing from the spirit and scope of the invention and it is intended that all such modifications and adaptations come within the scope of the appended claims. The various aspects and embodiments disclosed herein are for purposes of illustration and are not intended to be limiting, with the true scope and spirit of the invention being indicated by the appended claims.

The invention claimed is:

1. A diffusion cell comprising:
a donor compartment;
a receptor compartment comprising a cavity extending along a vertical axis of the receptor compartment, a first opening and a second opening, the donor compartment being insertable into and removable from the cavity of the receptor compartment; and
a tube passing through and generally perpendicular to the vertical axis of the receptor compartment, the tube comprising a length, a first end and a second end, a wall extending from the first end to the second end, a channel defined by the wall, and a slit in the wall, the tube configured for fluid flow along the channel from the first end towards the second end,
wherein the first end of the tube extends through the first opening of the receptor compartment, and the second end of the tube extends through the second opening of the receptor compartment.

2. The diffusion cell of claim 1, wherein the slit has a first open end positioned on an external surface of the wall facing the donor compartment, and an opposing second open end positioned on an internal surface of the wall facing the channel, and wherein the slit exposes the fluid in the channel to content permeating from the donor compartment.

3. The diffusion cell of claim 2, wherein the donor compartment comprises a first end and a second end, wherein the donor compartment comprises a cavity extending along a vertical axis of the donor compartment, wherein the cavity of the donor compartment comprises a first end and a second end, wherein the first end of the cavity of the donor compartment forms a first opening in the first end of the donor compartment, and wherein the second end of the cavity of the donor compartment forms a second opening in the second end of the donor compartment.

4. The diffusion cell of claim 3, wherein the cavity of the receptor compartment comprises an open end and a closed end.

5. The diffusion cell of claim 4, wherein the second end of the donor compartment is adjacent to the closed end of the cavity of the receptor compartment.

6. The diffusion cell of claim 5, wherein the second opening in the second end of the donor compartment is adjacent to the slit of the tube.

7. The diffusion cell of claim 1, wherein the diffusion cell is miniaturized.

8. The diffusion cell of claim 1, wherein the tube is insertable into the receptor compartment.

* * * * *